(12) United States Patent
An et al.

(10) Patent No.: US 11,345,049 B2
(45) Date of Patent: May 31, 2022

(54) GRASPING MECHANISM, ROBOT AND GRASPING DEVICE

(71) Applicants: SHANGHAI FLEXIV ROBOTICS TECHNOLOGY CO., LTD., Shanghai (CN); FLEXIV LTD., Cayman Islands (GB)

(72) Inventors: Ran An, Santa Clara, CA (US); Shiquan Wang, Santa Clara, CA (US)

(73) Assignees: SHANGHAI FLEXIV ROBOTICS TECHNOLOGY CO., LTD., Shanghai (CN); FLEXIV LTD., Cayman Islands (GB)

( * ) Notice: Subject to any disclaimer, the term of this patent is extended or adjusted under 35 U.S.C. 154(b) by 275 days.

(21) Appl. No.: 16/617,332

(22) PCT Filed: Nov. 20, 2019

(86) PCT No.: PCT/CN2019/119618
§ 371 (c)(1),
(2) Date: Nov. 26, 2019

(87) PCT Pub. No.: WO2021/097697
PCT Pub. Date: May 27, 2021

(65) Prior Publication Data
US 2021/0354315 A1 Nov. 18, 2021

(51) Int. Cl.
*B25J 15/08* (2006.01)
(52) U.S. Cl.
CPC ..................... *B25J 15/08* (2013.01)
(58) Field of Classification Search
CPC ...... B25J 15/08; B25J 15/0038; B25J 15/086; B25J 15/022

USPC ........................................................ 294/106
See application file for complete search history.

(56) References Cited

U.S. PATENT DOCUMENTS

| 8,973,958 | B2 * | 3/2015 | Allen Demers | B25J 15/022 |
| | | | | 294/106 |
| 9,327,412 | B2 | 5/2016 | Claffee et al. | |
| 9,757,690 | B2 * | 9/2017 | Slone | F01N 3/2033 |
| 9,782,902 | B1 * | 10/2017 | Kim | B25J 15/0009 |
| 10,265,862 | B1 * | 4/2019 | Alqasemi | B25J 15/0028 |
| 10,933,535 | B2 * | 3/2021 | Jiang | B25J 15/008 |

(Continued)

FOREIGN PATENT DOCUMENTS

| CN | 102328311 A | 1/2012 |
| CN | 110216703 A | 9/2019 |

(Continued)

OTHER PUBLICATIONS

International Search Report and Written Opinion dated Aug. 20, 2020 as received in PCT International Patent Appl. No. PCT/CN2019/119618.

*Primary Examiner* — Paul T Chin
(74) *Attorney, Agent, or Firm* — Dorsey & Whitney LLP

(57) ABSTRACT

A grasping mechanism includes a base and at least two linkage grasping assemblies. Each linkage grasping assembly includes a grasping member, a first rod and a second rod. The grasping member includes a grasping portion and a connecting portion. The first rod has a first end rotatably connected to the connecting portion and a second end rotatably connected to the base. The second rod has a first end rotatably connected to the connecting portion and a second end rotatably connected to the base.

20 Claims, 12 Drawing Sheets

(56) References Cited

U.S. PATENT DOCUMENTS

2010/0156127 A1* 6/2010 De Kervanoael .... B25J 15/0253
                                                         294/106
2018/0117773 A1* 5/2018 Odhner ................. B25J 15/024

FOREIGN PATENT DOCUMENTS

| GN | 103167937 A | 6/2013 |
| JP | 2011-224667 A * | 11/2011 |
| JP | 5434766 B2 | 3/2014 |
| WO | 2013075245 A1 | 5/2013 |
| WO | 2018162212 A1 | 9/2018 |

\* cited by examiner

GRASPING MECHANISM, ROBOT AND GRASPING DEVICE

TECHNICAL FIELD

The present disclosure relates to grasping structure technology, and in particular to a grasping mechanism, a robot and a grasping device.

BACKGROUND

Generally, when a gripper is used to catch an object, a grasping portion is moved by a finger linkage of the gripper to come into contact with or separate from the object to be grasped. The finger linkage of the gripper is disposed in a parallelogram shape which is suitable for grasping the object that has a flat external surface. However, the conventional gripper cannot be ensured to firmly grasp the object that has a ball shape or other complex shape.

SUMMARY

According to various embodiments of the present disclosure, a grasping mechanism, a robot and a grasping device are provided.

The technical solutions are shown as follows.

A grasping mechanism includes a base and at least two linkage grasping assemblies configured to cooperate with each other to grasp an object, each of the at least two linkage grasping assemblies including: a grasping member including a grasping portion and a connecting portion connected to each other; a first rod having a first end rotatably connected to the connecting portion and a second end rotatably connected to the base, a connecting line between a rotation center of the first end of the first rod and a rotation center of the second end of the first rod defining a first connecting line; a second rod having a first end rotatably connected to the connecting portion and a second end rotatably connected to the base, a connecting line between a rotation center of the first end of the second rod and a rotation center of the second end of the second rod defining a second connecting line; wherein a length of the first connecting line is constantly different from a length of the second connecting line, or the second rod is switchable between a first state in which a length of the second rod is kept constant and a second state in which the second rod is bent and deformed in such a way that the length of the first connecting line is different from the length of the second connecting line.

A robot includes a body and a grasping mechanism, the grasping mechanism including a base and at least two linkage grasping assemblies configured to cooperate with each other to grasp an object, each of the at least two linkage grasping assemblies including: a grasping member including a grasping portion and a connecting portion connected to each other; a first rod having a first end rotatably connected to the connecting portion and a second end rotatably connected to the base, a connecting line between a rotation center of the first end of the first rod and a rotation center of the second end of the first rod defining a first connecting line; a second rod having a first end rotatably connected to the connecting portion and a second end rotatably connected to the base, a connecting line between a rotation center of the first end of the second rod and a rotation center of the second end of the second rod defining a second connecting line; wherein a length of the first connecting line is constantly different from a length of the second connecting line, or the second rod is switchable between a first state in which a length of the second rod is kept constant and a second state in which the second rod is bent and deformed in such a way that the length of the first connecting line is different from the length of the second connecting line.

A grasping device includes a mounting base and a plurality of linkage grasping assemblies, wherein the plurality of linkage grasping assemblies are disposed in pairs facing each other and are arranged on the mounting base in an array, and the two opposing linkage grasping assemblies are configured to cooperate with each other to grasp an object, each of the plurality of linkage grasping assemblies including: a grasping member including a grasping portion and a connecting portion connected to each other; a first rod having a first end rotatably connected to the connecting portion and a second end rotatably connected to the base, a connecting line between a rotation center of the first end of the first rod and a rotation center of the second end of the first rod defining a first connecting line; a second rod having a first end rotatably connected to the connecting portion and a second end rotatably connected to the base, a connecting line between a rotation center of the first end of the second rod and a rotation center of the second end of the second rod defining a second connecting line; wherein a length of the first connecting line is constantly different from a length of the second connecting line, or the second rod is switchable between a first state in which a length of the second rod is kept constant and a second state in which the second rod is bent and deformed in such a way that the length of the first connecting line is different from the length of the second connecting line.

One or more embodiments are described further below by way of the drawings and specific embodiments. Other features, objects and benefits of the disclosure will be apparent to those skilled in the art from the description of the specification, drawings and claims.

Figure 1:
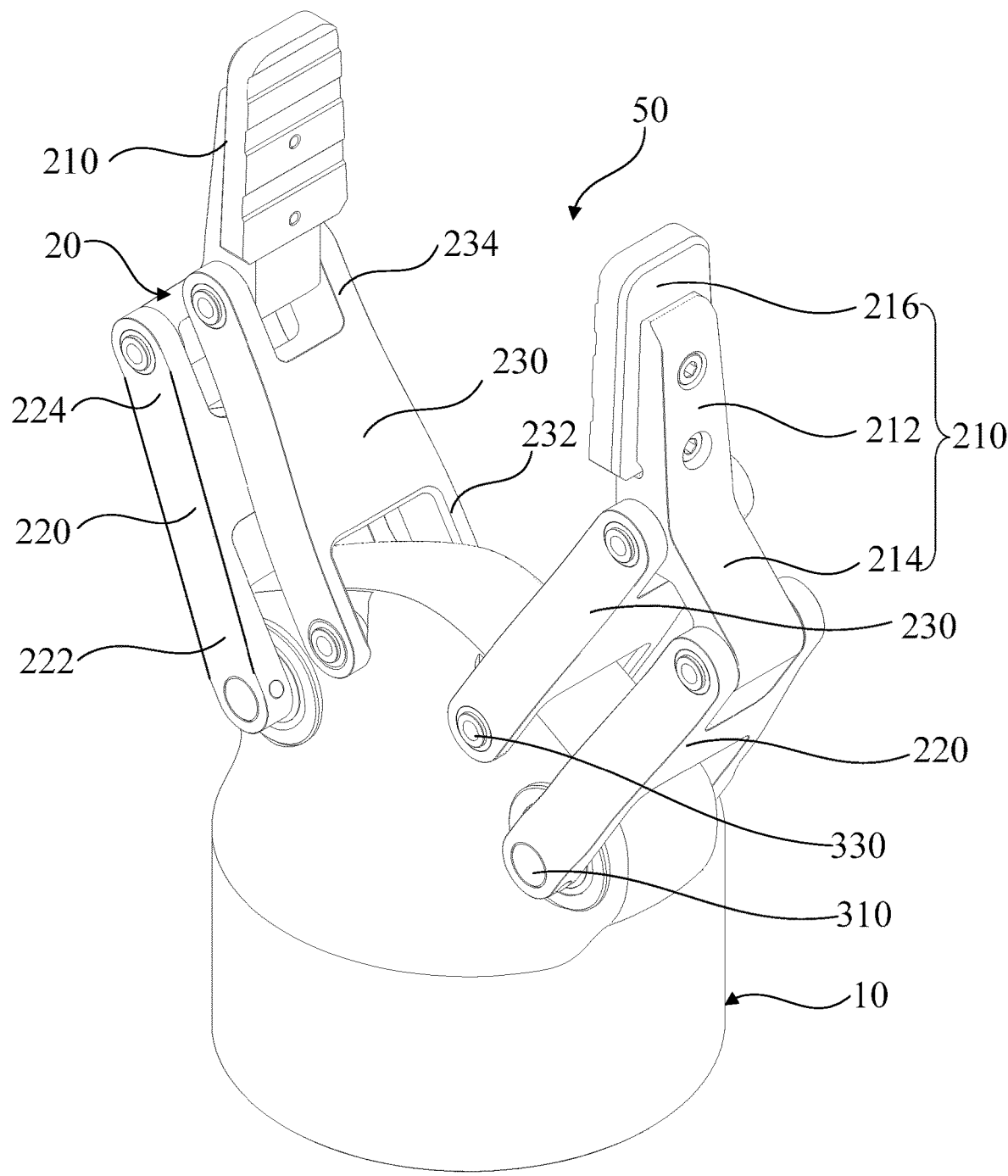
FIG. 1 is a schematic perspective view of a grasping mechanism according to one or more embodiments.

REFERENCE NUMERALS 02, object; 04, object;
10, base;
20, linkage grasping assembly; 210, grasping member; 212, grasping portion; 214, connecting portion; 216, contacting portion; 220, first rod; 222, first mounting portion; 224, third mounting portion; 230, second rod; 232, second mounting portion; 234, fourth mounting portion; 236, positioning projection; 238, positioning groove; 240, second rod; 242, first finger root portion; 244, second finger root portion; 246, elastic portion; 310, connecting shaft; 320, first bearing; 330, rotary shaft;
40, driving assembly; 410, power source; 420, screw rod; 430, nut; 440, first transmission rod; 450, second transmission rod;
50, grasping mechanism; 60, body; 70, mounting base.

For a better description and illustration of the embodiments and/or examples of the inventions disclosed herein, reference may be made to one or more of the accompanying drawings. Additional details or examples used to describe the accompanying drawings should not be considered as limiting the scope of any of the disclosed inventions, the presently described embodiments and/or examples, and the optimal patterns of these inventions that are presently understood.

DETAILED DESCRIPTION OF THE EMBODIMENTS

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

In the description of the present application, when an element is referred to as being "fixed to" or "provided in/on/at" another element, it may be directly or indirectly in/on/at the other element. When an element is referred to as being "connected to" another element, it may be directly or indirectly connected to the other element.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The "first", "second", "third" and "fourth" mentioned in the present invention do not represent a specific number and sequence, but are merely used to distinguish names.

Figure 2:
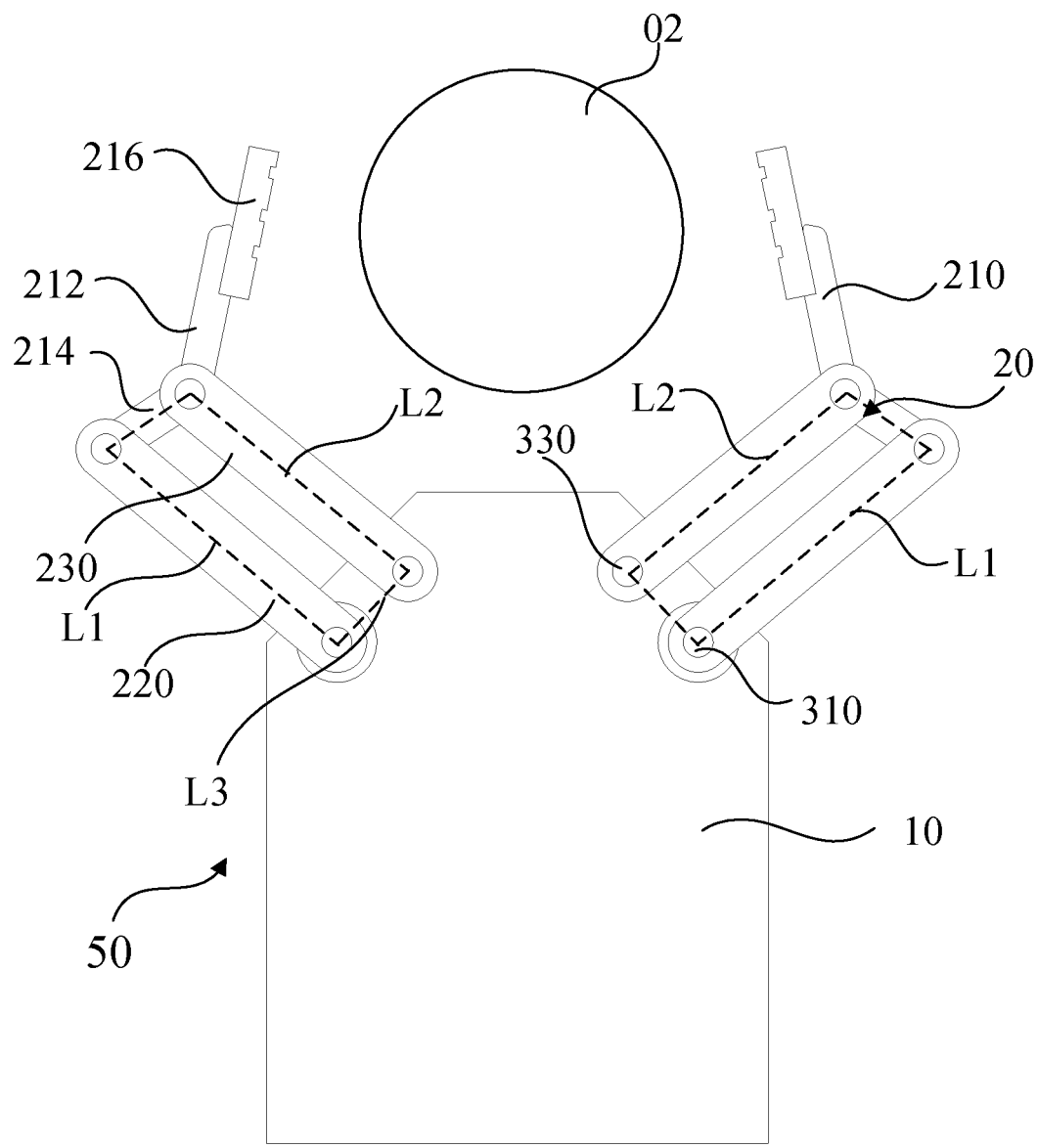
FIG. 2 is a schematic view of a grasping mechanism with grasping portions being in a first position according to one or more embodiments.
Figure 3:
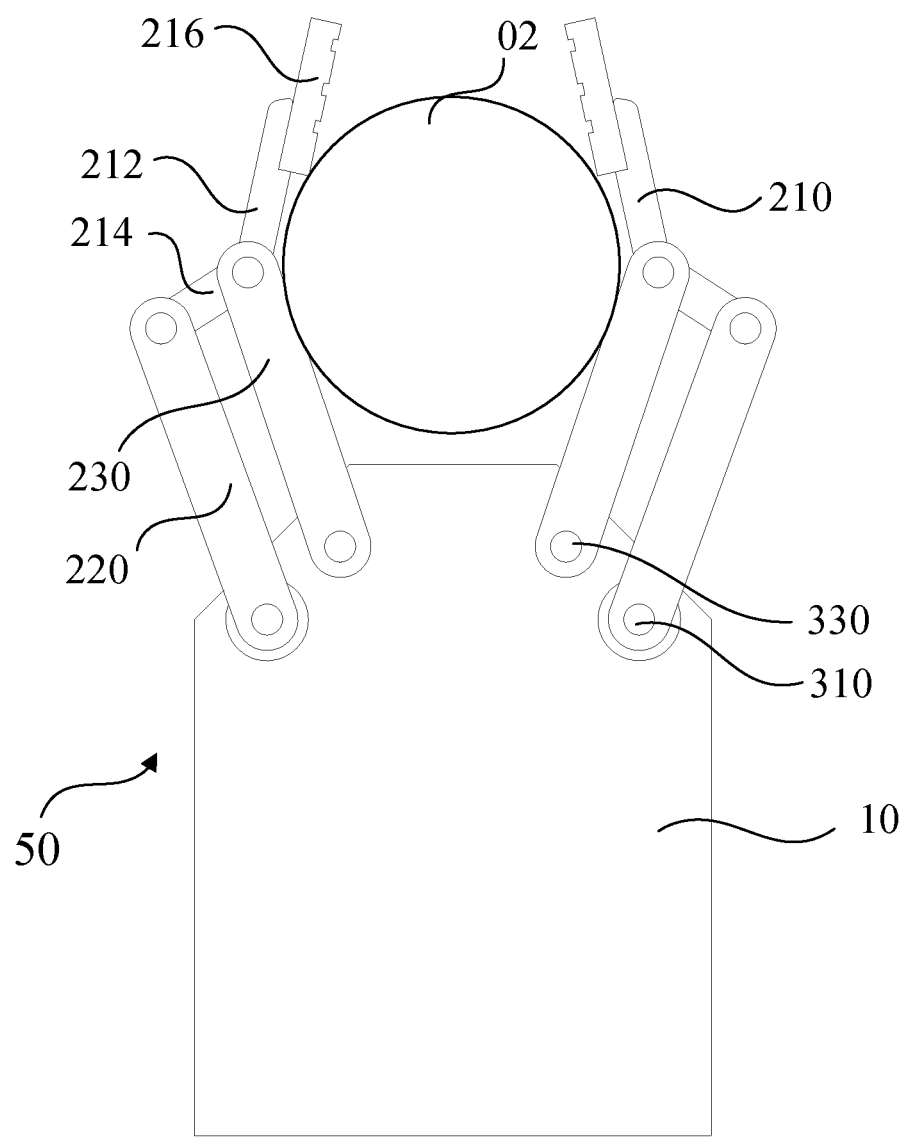
FIG. 3 is a schematic view of the grasping mechanism shown in FIG. 2 with the grasping portions being in a second position.

Referring to FIGS. 1, 2 and 3, a grasping mechanism 50 is provided by an embodiment of the present disclosure. The grasping mechanism 50 includes a base 10 and at least two linkage grasping assemblies 20. The at least two linkage grasping assemblies 20 can cooperate with each other to grasp an object.

In one of the embodiments, the linkage grasping assembly 20 includes a grasping member 210, a first rod 220, and a second rod 230. The grasping member 210 includes a grasping portion 212 and a connecting portion 214 connected to each other. A first end of the first rod 220 is rotatably connected to the connecting portion 214, and a second end of the first rod 220 is rotatably connected to the base 10. A connecting line between a rotation center of the first end of the first rod 220 and a rotation center of the second end of the first rod 220 defines a first connecting line L1. A first end of the second rod 230 is rotatably connected to the connecting portion 214, and a second end of the second rod 230 is rotatably connected to the base 10. A connecting line between a rotation center of the first end of the second rod 230 and a rotation center of the second end of the second rod 230 defines a second connecting line L2. In this embodiment, a length of the first connecting line L1 is constantly different from a length of the second connecting line L2.

In the aforementioned grasping mechanism 50, the linkage grasping assembly 20 may be rotated to approach or move away from the object to be grasped 02. Since the length of the first connecting line L1 is constantly different from the length of the second connecting line L2, an angle of the grasping portion relative to the object to be grasped 02 is gradually changed when the linkage grasping assembly 20 rotates towards the object to be grasped 02, so that the grasping portion 212 is able to hold the object to be grasped 02 (as shown in FIG. 3). Even if the object to be grasped 02 has a ball shape or other complex shape, it can still be firmly grasped, and the versatility and flexibility of the linkage grasping assembly 20 are improved.

In contrast, a finger linkage of a conventional gripper has a parallelogram shape, which forms a constant angle relative to a contacting part of an object to be grasped. In this embodiment, the quadrilateral formed by successively connecting the rotation centers of the first end of the first rod 220, the second end of the first rod 220, the second end of the second rod 230 and the first end of the second rod 230 is not a parallelogram. Specifically, referring to FIGS. 2 and 3, the grasping portion 212 rotates from a first position of FIG. 2 to a second position of FIG. 3, and the grasping portion 212 correspondingly rotates for a certain angle with respect to the object to be grasped 02, so as to firmly grasp the object to be grasped 02.

Further, referring to FIGS. 1, 2 and 3, in this embodiment, a first end of the connecting portion 214 is rotatably connected to the first end of the first rod 220, a second end of the connecting portion 214 is rotatably connected to the first end of the second rod 230, and the second end of the connecting portion 214 is fixed to the grasping portion 212. In other words, during rotation of the first rod 220, the grasping member 210, and the second rod 230, a connecting line L3 connecting between the rotation center of the second end of the first rod member 220 and the rotation center of the second end of the second rod member 230 is constant, and the connecting portion 214 rotates for a certain angle with respect to the connecting line L3. Accordingly, the grasping portion 212 fixed to the connecting portion 214 rotates for a certain angle, so that the grasping mechanism is able to be flexibly adapted to firmly grasp an object with a complex shape.

In this embodiment, the length of the first connecting line is constantly greater than the length of the second connecting line. The grasping portion 212 is located at a side close to the second rod 230, and the second rod 230 is located at an inner side relative to the first rod 220, wherein the inside side refers to a side closer to the object to be grasped. When the grasping mechanism is utilized to catch the object to be grasped 02 which has a non-flat external surface (for example, the external surface of the object is a curved surface or other complex shape), a rod section of the second rod 230 can cooperate with the grasping portion 212 to grasp the object to be grasped 02, resulting in a more secure and stable grasping. The difference between the lengths of L1 and L2 can be selected flexibly according to the shape of the object to be grasped. Alternatively, in some embodiments, the second rod on the inner side may also be longer than the first rod on an outer side, depending on the shape of the object to be grasped.

Figure 9:
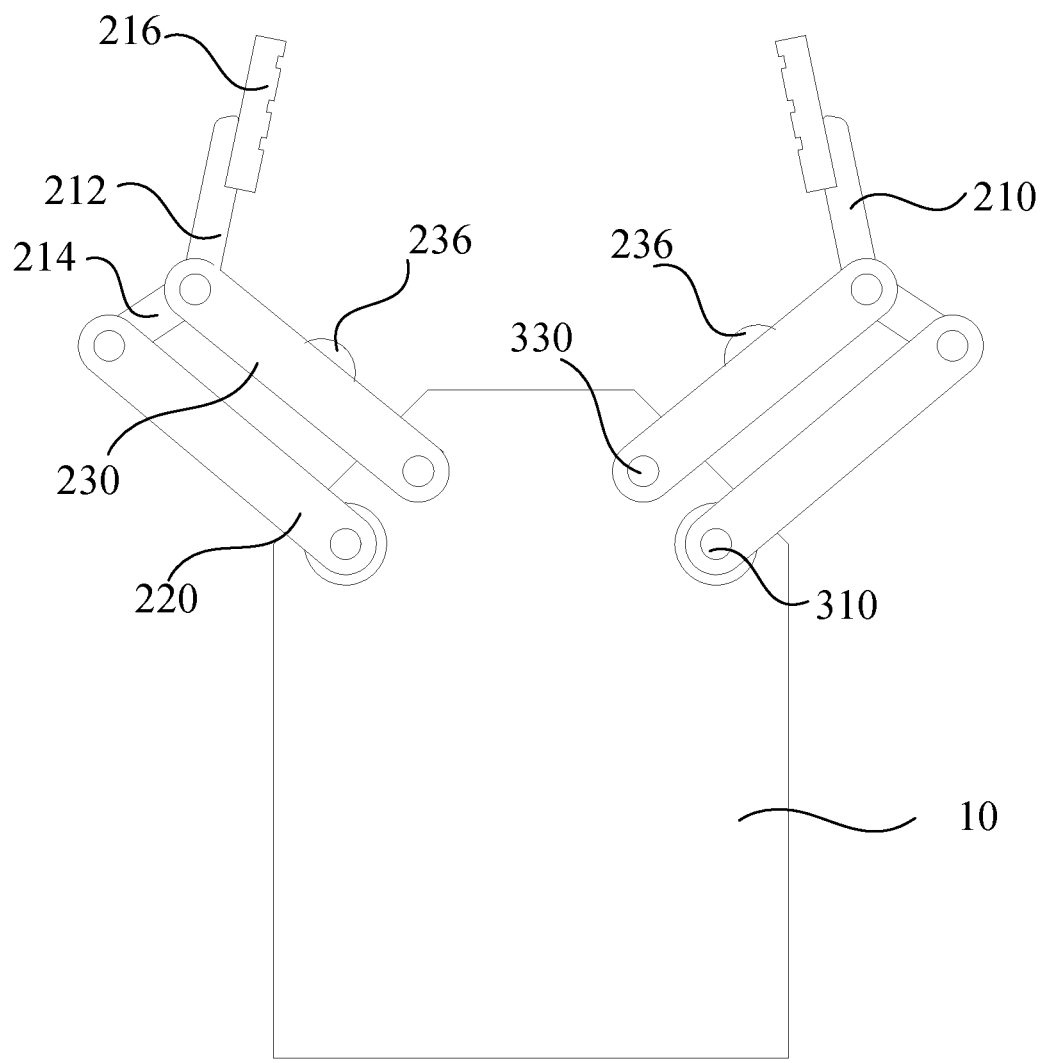
FIG. 9 is a schematic view of a grasping mechanism according to one or more embodiments.
Figure 10:
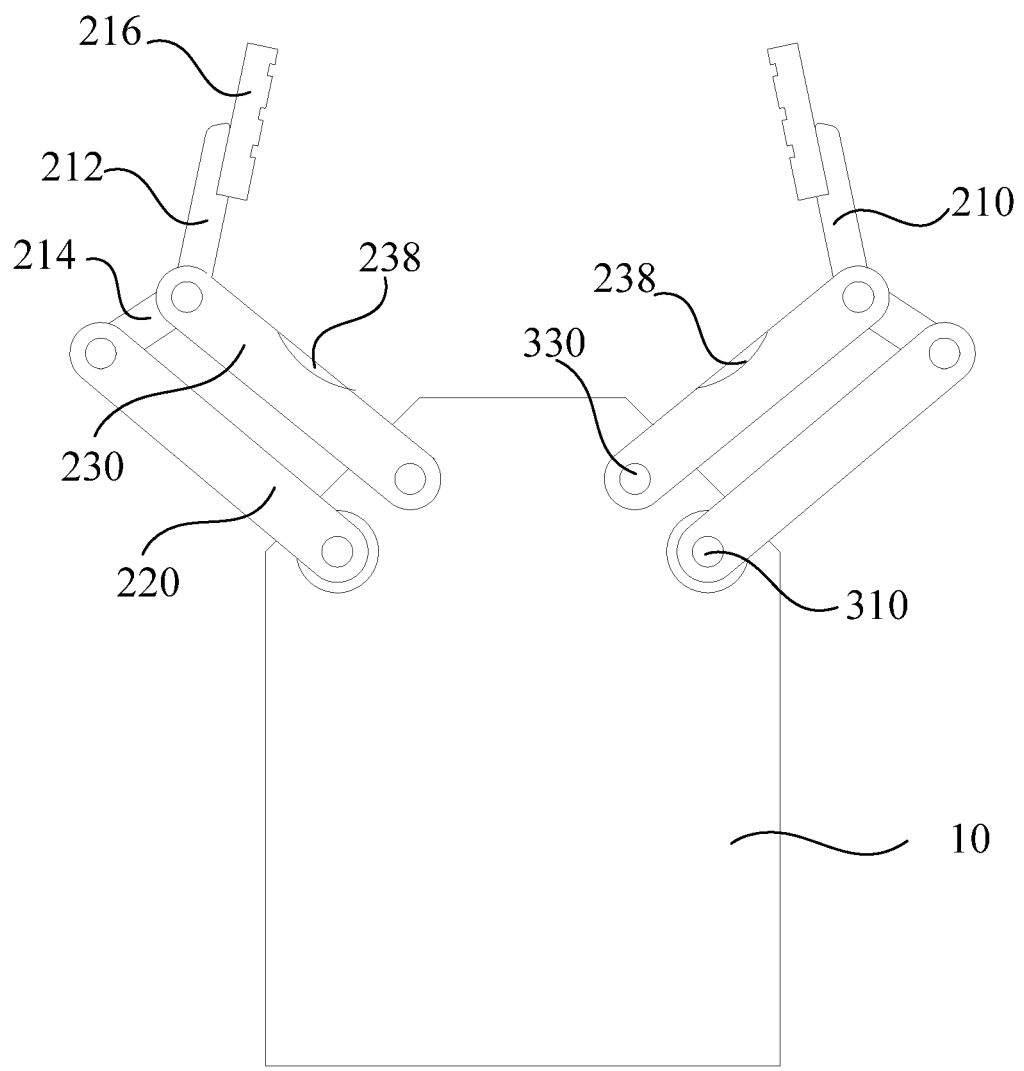
FIG. 10 is a schematic view of a grasping mechanism according to one or more embodiments.

The second rod 230 in this embodiment of FIG. 1 is a straight rod. In other embodiments, the second rod 230 may also be a bent rod. Referring to FIGS. 9 and 10, an inner surface of the second rod may be provided with a positioning groove 238 or a positioning projection 236. Due to the positioning groove 238 or the positioning projection 236, the object to be grasped can be positioned, and the stability of the grasping is improved.

Figure 4:
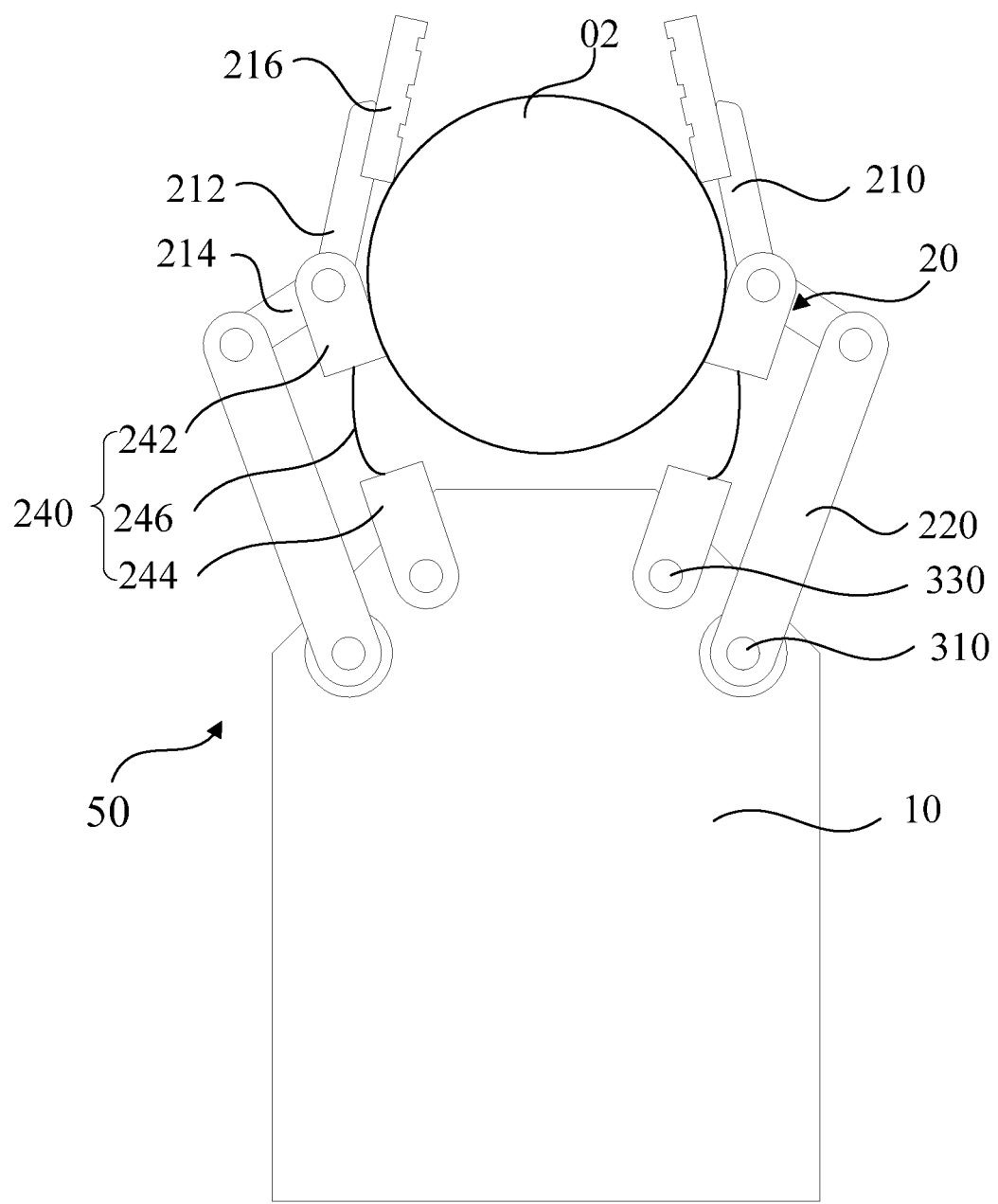
FIG. 4 is a schematic view of a grasping mechanism in a second state according to another or more embodiments.
Figure 5:
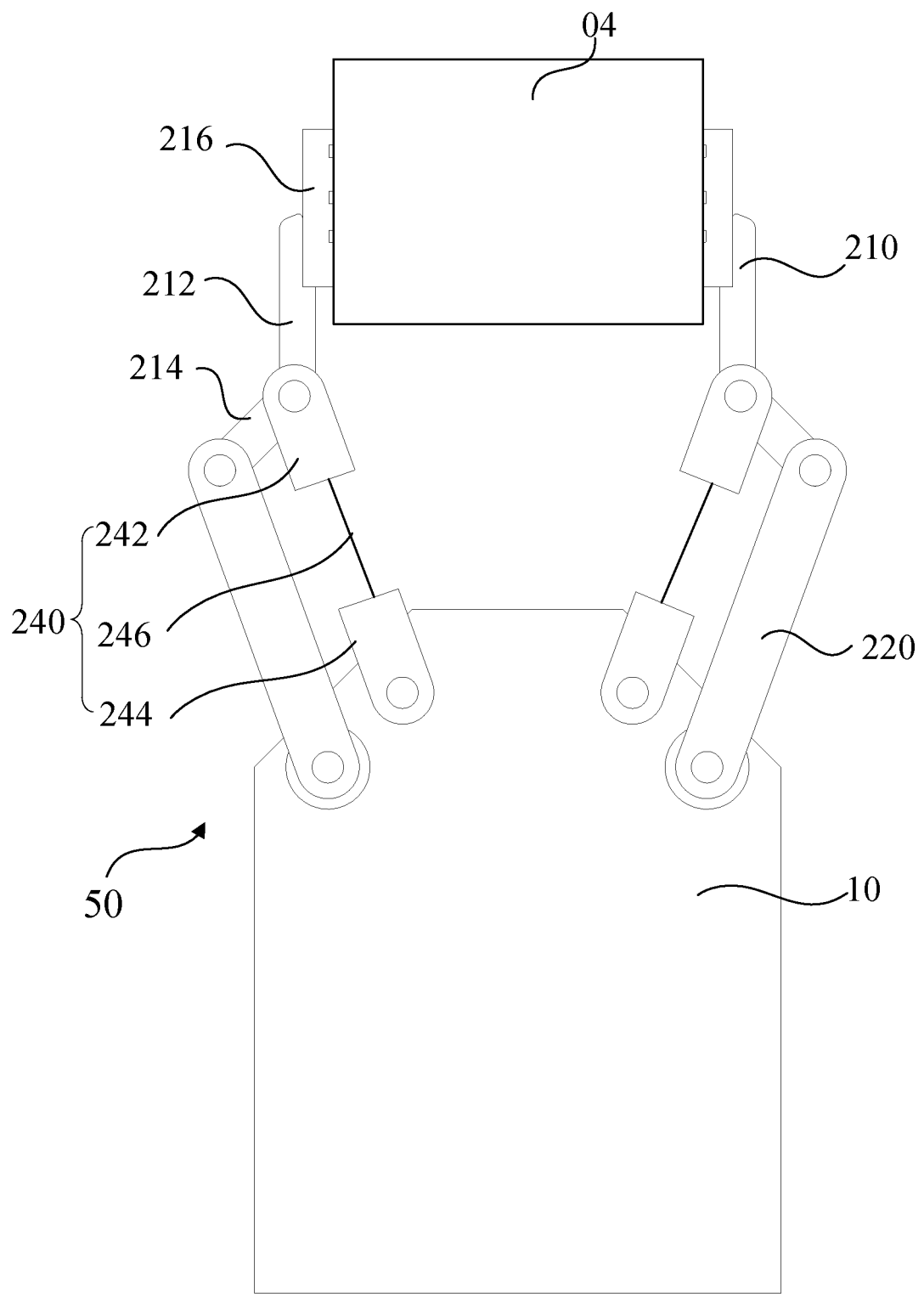
FIG. 5 is a schematic view of a grasping mechanism in a first state according to another or more embodiments.

Referring to FIGS. 4 and 5, in another embodiment of the present disclosure, the second rod 240 is switchable between a first state and a second state. Referring to FIG. 5, in the first state, the length of the second rod is kept constant. The first state is a state in which the object has not been grasped by the second rod 240 or the grasped object has a flat external surface. Referring to FIG. 4, in the second state, the second rod 240 is bent and deformed, so that the length of the first connecting line is different from the length of the second connecting line. The second state is a state in which the rod section of the second rod member 240 has a deformation caused by the press of the object to be grasped. A connecting line between a rotation center of the first end of the first rod 220 and a rotation center of the second end of the first rod 220 defines a first connecting line, and a connecting line between a rotation center of the first end of the second rod 240 and a rotation center of the second end of the second rod 240 defines a second connecting line. In the second state, the second rod 240 is bent and deformed, so that the length of the first connecting line is different from the length of the second connecting line. When the linkage grasping assembly 20 rotates towards the object to be grasped 02, the angle of the grasping portion relative to the object to be grasped 02 is gradually changed, so that the grasping portion 212 is able to hold and firmly grasp the object to be grasped 02. Thus, the versatility and flexibility of the linkage grasping assembly 20 are improved.

It should be noted that, although not shown, in some other embodiments, it is possible to configure the first rod or the second rod to be a length-adjustable structure. For example, the first rod and/or the second rod may be a retractable rod. The length of the first rod and/or the second rod is adjusted automatically or manually as required, so that the length of the first connecting line is different from the length of the second connecting line, and thus the grasping mechanism is applicable to objects of different shapes and sizes.

In FIG. 4, when the grasping portion 212 cooperates with the first end of the second rod 240 to grasp the ball, the second rod member 240 is bent and deformed, so that the length of the first connecting line is greater than the length of the second connecting line, and the angle of the grasping portion 212 relative to the object to be grasped 02 is changed. Thus, the grasping mechanism may be adapted to firmly grasp an object with a complex shape, such as a ball and the like. In FIG. 5, when the object to be grasped 04 with a flat external surface is only contacted by the grasping portion 212, the length of the second rod 240 remains unchanged under the action of tension, and meanwhile the length of the first connecting line and the length of the second connecting line are the same as those in the first state. For example, in this case, the length of the first connecting line and the length of the second connecting line may be kept constantly equal.

Further, referring to FIG. 4, when the linkage grasping assembly 20 is in a state of grasping the object 02, the length of the first connecting line is greater than the length of the second connecting line. The difference between the lengths of the first connecting line and the second connecting line can be selected flexibly according to the shape of the object to be grasped 02. In this embodiment, when the object is grasped, the length of the first connecting line is greater than the length of the second connecting line, and the grasping portion 212 is located on the side close to the second rod 240. When the grasping mechanism is utilized to catch the object to be grasped 02 which has a non-flat external surface (for example, the external surface of the object is a curved surface or other complex shape), a rod section of the second rod 240 cooperating with the grasping portion 212 can be utilized to grasp the object to be grasped 02, resulting in a more secure and stable grasping.

Specifically, referring to FIG. 4, in one embodiment, the second rod 240 includes a first finger root portion 242, an elastic portion 246, and a second finger root portion 244 that are successively connected. The first finger root portion 242 is rotatably connected to the connection portion 214, and the second finger root portion 244 is rotatably connected to the base 10. In the second state, the first finger root portion 242 and/or the second finger root portion 244 contacts and presses the object to be grasped, and the elastic portion 246 is bent and deformed under a counterforce of the object, so that the distance between the two ends of the second rod 240 becomes shorter. That is, the length of the first connecting line is greater than the length of the second connecting line, such that the angle adjustment of the grasping portion 212 during movement is achieved to facilitate the grasping portion 212 to firmly grasp the object to be grasped 02 which has a non-flat external surface. In some embodiments, the elastic portion 246 is an elastic metal sheet. In other embodiments, the elastic portion 246 may also be other parts that are not prone to tensile deformation but are bendable and deformable.

Referring to FIGS. 1, 2 and 4, in one or more embodiments, the grasping member 210 further includes a contacting portion 216 connected to the grasping portion 212 and located on a side corresponding to a grasping surface of the grasping portion 212. The connecting portion 214 and the grasping portion 212 may be selected from metal material with good strength, and the contacting portion 216 may be selected from material different from that of the grasping portion 212, such as rubber and plastic with higher friction coefficient. The contacting portion 216 contacts the object to be grasped, thus the friction force therebetween is increased, and the stability of the grasping is improved. In other embodiments, the object may also be grasped directly by the grasping portion, and the grasping portion is able to firmly grasp the object by means of surface treatment on the grasping surface of the grasping portion.

Referring to FIGS. 1 and 4, in one embodiment, the grasping portion 212 is connected to the connecting portion 214 at a blunt angle. A blunt angle is formed between the grasping portion 212 and the second rod 230 or 240 to form a grasping space. The grasping portion 212 and the connecting portion 214 are integrally formed, and the connecting portion 214 rotates and drives the grasping portion 212 to rotate synchronously. Further, the rotation center of the second end of the first rod 220 and the rotation center of the second end of the second rod 230 or 240 are arranged one above another in a height direction, the connecting line L3 which connects the rotation center of the second end of the first rod 220 and the rotation center of the second end of the second rod 230 or 240 is inclined, and the rotation center of the second end of the second rod 230 or 240 is located at an upper end of the connecting line L3, and the rotation center of the second end of the first rod 220 is located at an lower end of the connecting line L3.

Referring to FIGS. 1, 2, 4, 6 and 7, in one or more embodiments, the grasping mechanism 50 further includes a driving assembly 40. The first rod 210 or the second rod 230 or 240 may be driven by the driving assembly 40 to rotate, so that the linkage grasping assembly 20 rotates relative to the base 10. The driving assembly 40 may be installed inside the base 10. For example, the first rod 210 may be used as an active rod, and the driving assembly 40 drives the first rod 210 to rotate. The second rod 230 or 240 may follow the rotation of the first rod 210 to rotate with respect to the base 10, such that the grasping portion 212 may be moved closer to or further away from the object to be grasped. In other embodiments, the second rod 230 or 240 can be used as an active rod, which will not be described herein.

Figure 6:
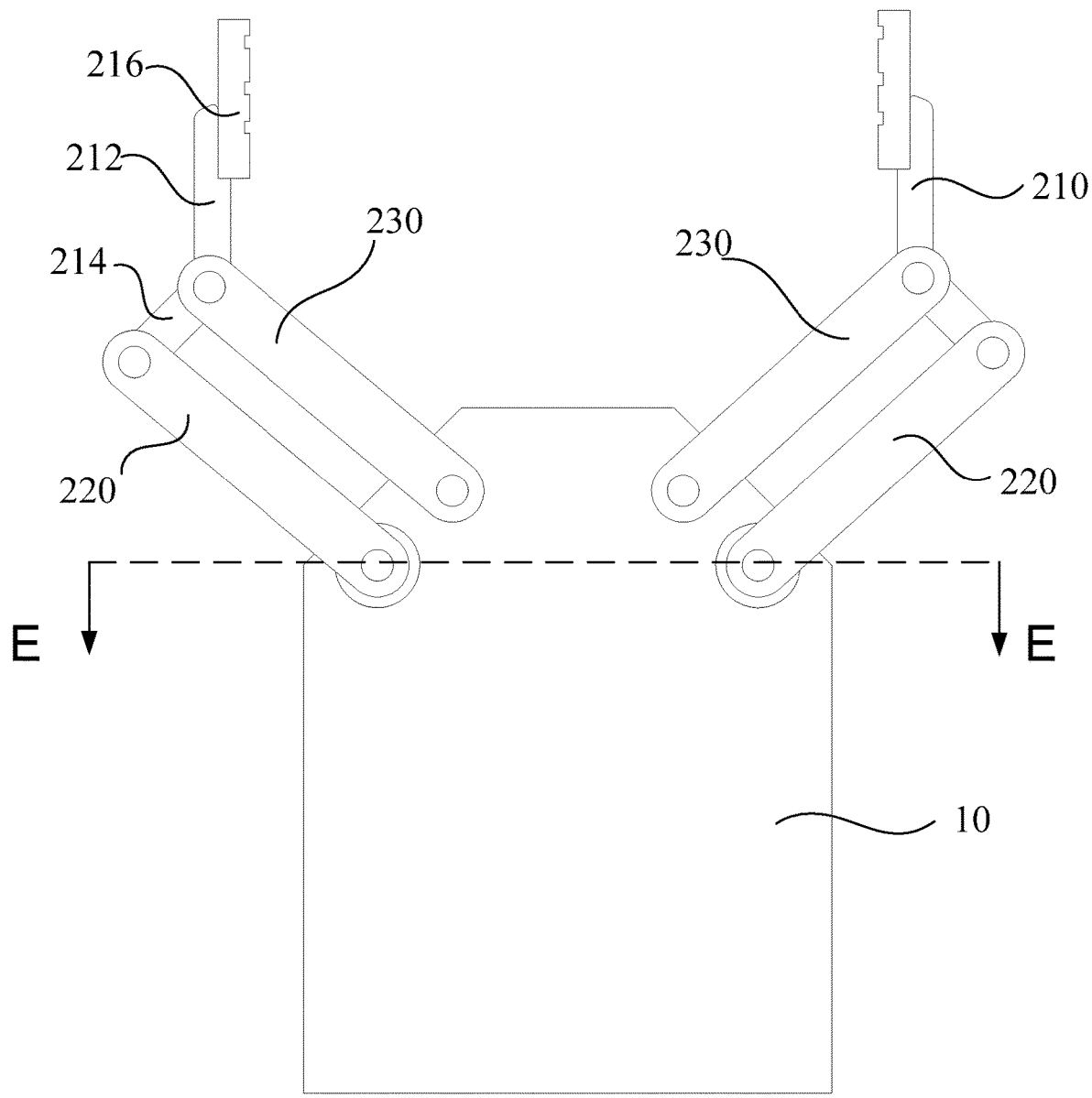
FIG. 6 is a schematic plan view of a grasping mechanism according to one or more embodiments.
Figure 7:
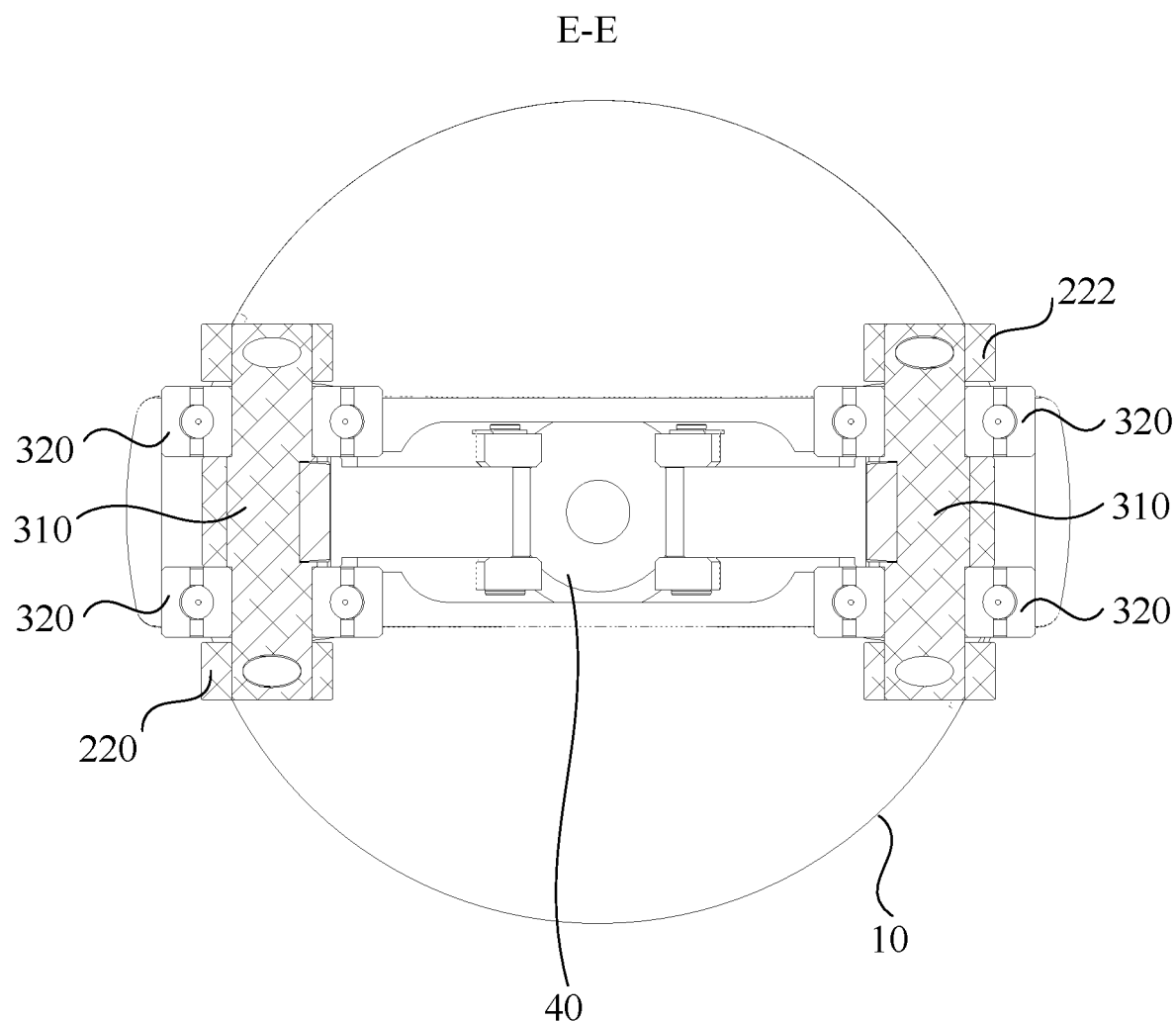
FIG. 7 is a schematic cross-sectional view taken along line E-E in FIG. 6.

Further, referring to FIGS. 6 and 7, the linkage grasping assembly 20 further includes a connecting shaft 310 and a first bearing 320. A first mounting hole (not labelled) is defined on the base 10, the first bearing 320 is mounted in the first mounting hole, the connecting shaft 310 is mounted on the first bearing 320 and sealingly fits with the first bearing 320. An end of the connecting shaft 310 extends out of the first mounting hole. The second end of the first rod 220 is fixed to the ends of the connecting shaft 310, and the connecting shaft 310 is connected to the driving assembly 40. The driving assembly 40 drives the connecting shaft 310 to rotate, and the connecting shaft 310 drives the first rod 220 to rotate synchronously, so as to drive the grasping member 210 and the second rod 230 or 240 to rotate. The first bearing 320 sealingly fits with the connecting shaft 310, so as to prevent water outside the base 10 from entering the base 10 through the first mounting hole, thus improving the waterproof performance of the grasping mechanism 50. In this embodiment, the first rod 220 is rotatably connected to the base 10 through the first bearing 320 and the connecting shaft 310, and has a good waterproof performance, which may be applied to any one of the above-mentioned grasping mechanisms 50, and may also be applied to other devices that require waterproof. For example, it can be applied to the conventional gripper of parallelogram structures, so as to improve the waterproof performance of the conventional gripper of parallelogram structures.

Specifically, the connecting shaft 310 is connected to an inner ring of the first bearing 320 by interference fit, and an outer ring of the first bearing 320 is received in the first mounting hole by interference fit. Thus, sealing fit between the first bearing 320 and the base 10, as well as between the connecting shaft 310 and the first bearing can be achieved. The inner ring of the first bearing 320 and the outer ring of the first bearing 320 are rotatably fitted by rolling elements. When the driving assembly 40 drives the connecting shaft 310 to rotate, the first rod 220 may rotate with respect to the base 10 along with the connecting shaft 310.

In one embodiment, the linkage grasping assembly 20 includes two first bearings 320. The connecting shaft 310 is mounted on the two first bearings 320, and two ends of the connecting shaft 310 extend out of the two first mounting holes, respectively. The second end of the first rod 220 includes two first mounting portions 222, and the two first mounting portions 222 are respectively fixed to the two ends of the connecting shaft 310. The connecting shaft 310 is assembled through the two first bearings 320, the two ends of the connecting shaft 310 extend out of the base 10 via the first mounting holes after extending out of the first bearings 320, and then are fixed to the first mounting portions 222 of the first rod 220. Referring to FIG. 1, the two first mounting portions 222 are spaced apart. Both sides of the base 10 define first mounting holes, and the two first mounting portions 222 are respectively located on both sides of the base 10 and fixed to the two ends of the connecting shaft 310, so that the first rod 220 rotates with the rotation of the connecting shaft 310. The first rod 220 is sleeved on the base 10 through two first mounting portions 222, and the two first mounting portions 222 are fixed to the two ends of the connecting shaft 310, which results in a stable installation and a smooth rotation.

Referring to FIGS. 1 and 2, in one or more embodiments, the linkage grasping assembly 20 further includes a rotary shaft 330 disposed on an outer wall of the base 10, and the second end of the second rod 230 or 240 is rotatably connected to the rotary shaft 330. In other embodiment, a hinge base may be disposed on the outer wall of the base 10, and the second rod 230 or 240 is rotatably connected to the hinge base so as to be rotatably connected to the base 10.

Further, referring to FIG. 1, the second end of the second rod 230 or 240 includes two second mounting portions 232, which are rotatably connected to the rotary shafts 330 on both sides of the base, which results in a stable installation and a smooth rotation.

Referring to FIG. 1, in one or more embodiments, the first end of the first rod 220 includes two opposing third mounting portions 224. The first end of the second rod 230 or 240 includes two opposing fourth mounting portions 234. The first end of the connecting portion 214 is disposed between the two third mounting portions 224 and rotatably connected to the two third mounting portions 224 respectively, and the second end of the connecting portion 214 is disposed between the two fourth mounting portions 234 and rotatably connected to the two fourth mounting portions 234 respectively. The two third mounting portions 224 are spaced apart to form a mounting space, and the two fourth mounting portions 234 are spaced apart to form a mounting space. Two ends of the connecting portion 214 are respectively located in the two mounting spaces. The end of the connecting portion 214 may be rotatably connected to the third mounting portion 224 or the fourth mounting portion 234 in a shaft-hole fitting manner.

Figure 8:
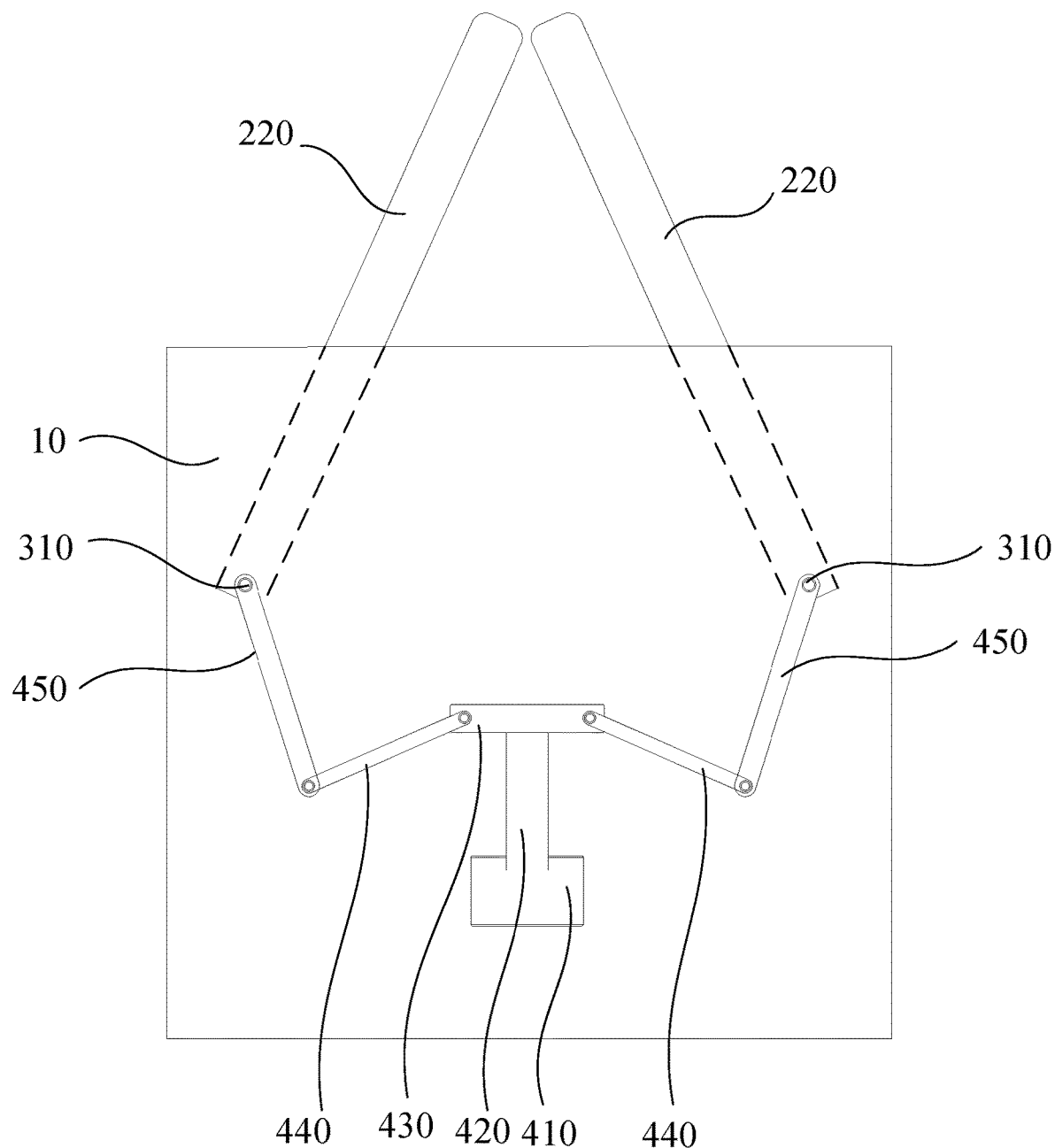
FIG. 8 is a schematic view of a driving assembly of a grasping mechanism according to one or more embodiments.

Referring to FIG. 8, in one or more embodiments, the driving assembly 40 includes a power source 410, a screw rod 420, a nut 430, at least two first transmission rods 440, and at least two second transmission rods 450. The power source 410 is connected to the screw rod 420, and the nut 430 is sleeved on the screw rod 420 and can reciprocate along the screw rod 420. One end of the first transmission rod 440 is rotatably connected to the nut 430, and the other end of the first transmission rod 440 is rotatably connected to the second transmission rod 450. The second transmission rod 450 is fixed to the connecting shaft 310. The power source 410 provides power to the screw rod 420 for rotation, and the power source 410 may be a motor. The screw 420 rotates to drive the nut 430 and one end of the first transmission rod 440 to perform reciprocating linear motion. Thus, the second transmission rod 450 and the connecting shaft 310 are driven to rotate relative to the base 10, and the first rod 220, or the second rod 230 or the second rod 240 fixed to the connecting shaft 310 are driven to rotate, such that the grasping portion 212 is brought towards or away from the object to be grasped. In other embodiments, the driving assembly 40 of other structures, such as a gear transmission mechanism, a worm-gear transmission mechanism, a hydraulic/pneumatic transmission mechanism, or the like, may be adopted to drive the first rod 220, or the second rod 230, or the second rod 240 to rotate.

In some embodiments, referring to FIG. 1, in one embodiment, the grasping mechanism 50 includes two linkage grasping assemblies 20 according to any one of the above embodiments, and the two linkage grasping assemblies 20 are arranged opposite to each other. The two second rods 230 or 240 are located on the inner side of the two linkage grasping assemblies 20. The object is grasped by cooperation of the two linkage grasping assemblies 20, and the angle of the grasping portion 212 of the linkage grasping assembly 20 is variable to be adapted to grasping of the object with a ball shape or other complex structure. In other embodiments, the number of the linkage grasping assembly 20 may be increased as desire, such as three, four, or more than four. The three, four, or more than four linkage grasping assemblies 20 are circumferentially arranged, and the grasping portions 212 thereof cooperate with each other to achieve grasping of the object.

Figure 11:
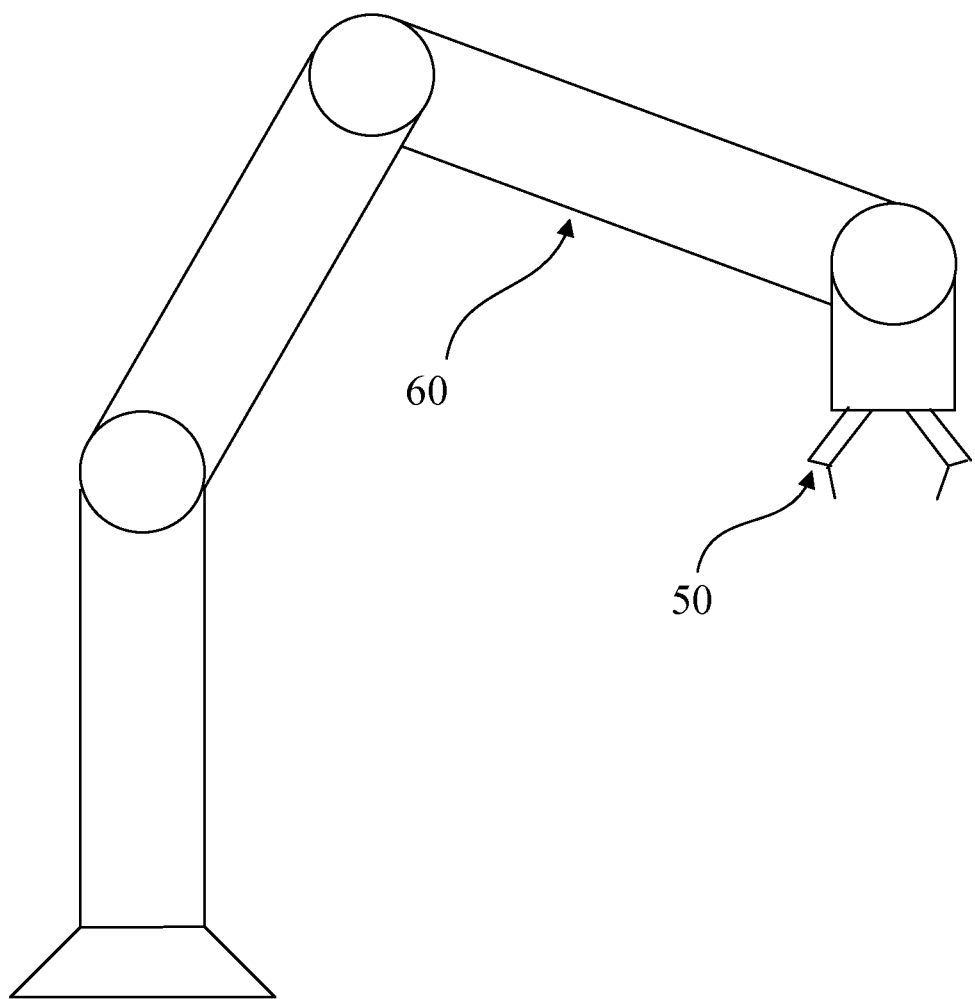
FIG. 11 is a schematic view of a robot according to one or more embodiments.

Referring to FIGS. 1 and 11, a robot is provided by another embodiment of the present disclosure. The robot includes a body 60 and a grasping mechanism 50 according to any one of the above embodiments. The body 60 includes a plurality of robotic links that are successively connected and a plurality of joint actuators for connecting adjacent robotic links. The grasping mechanism 50 includes a base 10 and at least two linkage grasping assemblies 20. The base 10 is connected to the body 60, and the at least two linkage grasping assemblies 20 are rotatably connected to the base 10, respectively. The at least two linkage grasping assemblies 20 cooperate to grasp an object.

The linkage grasping assembly 20 includes a grasping member 210, a first rod 220, and a second rod 230 or 240. The grasping member 210 includes a grasping portion 212 and a connecting portion 214 connected to each other. A first end of the first rod 220 is rotatably connected to the connecting portion 214, and a second end of the first rod 220 is rotatably connected to the base 10. A connecting line between a rotation center of the first end of the first rod 220 and a rotation center of the second end of the first rod 220 defines a first connecting line. A first end of the second rod 230 or 240 is rotatably connected to the connecting portion 214, and a second end of the second rod 230 or 240 is rotatably connected to the base 10. A connecting line between a rotation center of the first end of the second rod 230 or 240 and a rotation center of the second end of the second rod 230 or 240 defines a second connecting line. The length of the first connecting line is constantly different from the length of the second connecting line. In some embodiments, the second rod 240 is switchable between a first state and a second state. In the first state, the length of the second rod 240 is kept constant. In the second state, the second rod 240 is bent and deformed, so that the length of the first connecting line is different from the length of the second connecting line.

The robot adopts the grasping mechanism 50 described in any one of the above embodiments as the grasping mechanism at the end to achieve the grasping of the object, and has the advantages of the grasping mechanism 50 described in the corresponding embodiment, which will not be described here.

FIG. 11 is merely an exemplary embodiment of a robot. In other embodiment, the robot may include more or fewer assemblies. For example, the robot may also include an I/O device, a network access device, a communication bus, a processor, a memory, an actuator, and a sensor.

It should be understood that the grasping mechanism 50 provided herein may also be used in fields other than robots, such as packaging equipment, transport equipment, and the like, and is not limited herein.

Figure 12:
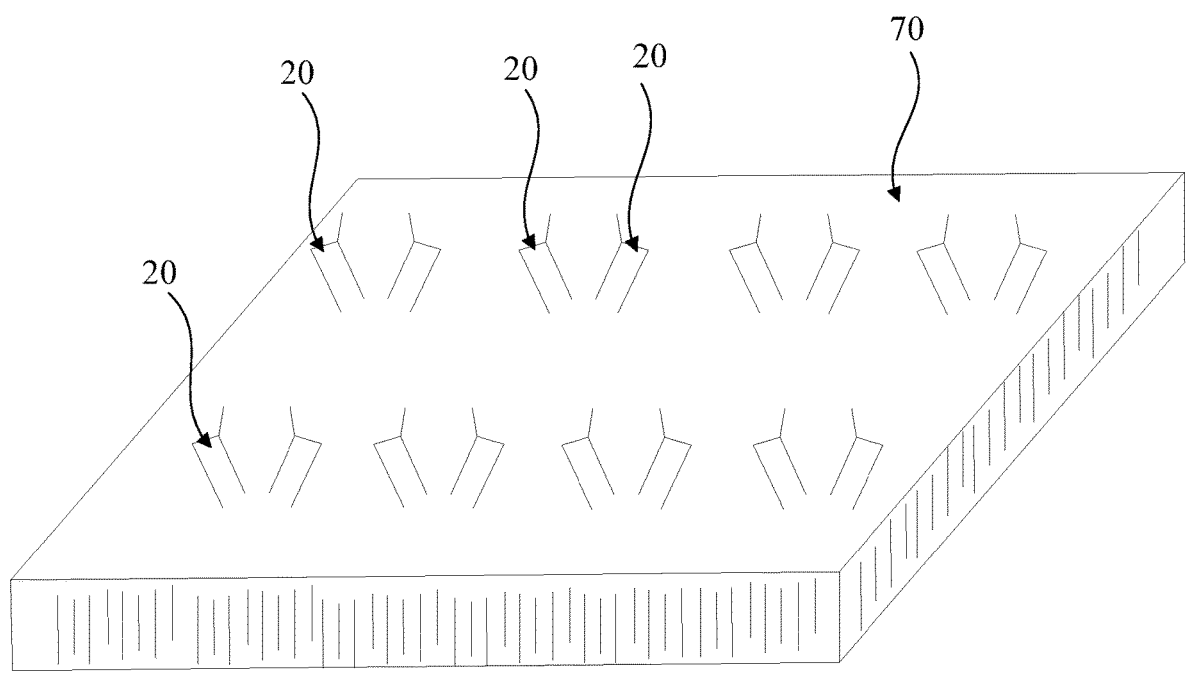
FIG. 12 is a schematic view of a grasping device according to one or more embodiments.

Referring to FIG. 12, a grasping device is provided according to an embodiment of the present disclosure, which includes a mounting base 70 and a plurality of linkage grasping assemblies 20 according to any one of the above embodiments. The plurality of linkage grasping assemblies 20 are disposed in pairs facing each other and are arranged on the mounting base 70 in an array, and the two opposing linkage grasping assemblies 20 are configured to cooperate with each other to grasp an object.

The linkage grasping assembly 20 includes a grasping member 210, a first rod 220, and a second rod 230 or 240. The grasping member 210 includes a grasping portion 212 and a connecting portion 214 connected to each other. A first end of the first rod 220 is rotatably connected to the connecting portion 214, and a second end of the first rod 220 is rotatably connected to the base 10. A connecting line between a rotation center of the first end of the first rod 220 and a rotation center of the second end of the first rod 220 defines a first connecting line. A first end of the second rod 230 or 240 is rotatably connected to the connecting portion 214, and a second end of the second rod 230 or 240 is rotatably connected to the base 10. A connecting line between a rotation center of the first end of the second rod 230 or 240 and a rotation center of the second end of the second rod 230 or 240 defines a second connecting line. The length of the first connecting line is constantly different from the length of the second connecting line. In some embodiments, the second rod 240 is switchable between a first state and a second state. In the first state, the length of the second rod 240 is kept constant. In the second state, the second rod 240 is bent and deformed, so that the length of the first connecting line is different from the length of the second connecting line.

In the grasping device, the plurality of linkage grasping assemblies 20 according to any one of the above embodiments are arranged in an array on the mounting base 70 and are disposed in pairs facing each other. The two opposing linkage grasping assemblies 20 are configured to cooperate with each other to grasp an object, so that simultaneous grasping or releasing of a plurality of objects on a standardized production line can be achieved.

Referring to FIGS. 1 to 5, the linkage grasping assembly 20 approaches or moves away from the object to be grasped 02. Since the length of the first connecting line L1 is constantly different from the length of the second connecting line L2, an angle of the grasping portion relative to the object to be grasped 02 is gradually changed when the linkage grasping assembly 20 rotates towards the object to be grasped 02, so that the grasping portion 212 is able to hold the object to be grasped 02. When the object to be grasped 02 has a ball shape or other complex shape, it can be firmly grasped, and the versatility and flexibility of the grasping device are improved. As an alternative, the second rod 240 is switchable between a first state and a second state. In the first state, the length of the second rod 240 is kept constant. The first state is a state in which the object has not been is grasped by the second rod 240 or the grasped object has a flat external surface. Referring to FIG. 4, in the second state, the second rod 40 is bent and deformed, so that the length of the first connecting line is different from the length of the second connecting line. The second state is a state in which the second rod 240 is grasping an object which has a non-flat external surface (for example, a ball shape or other complex shape). In the second state, the second rod 40 is bent and deformed, so that the length of the first connecting line is different from the length of the second connecting line. When the linkage grasping assembly 20 rotates towards the object to be grasped 02, the angle of the grasping portion relative to the object to be grasped 02 is gradually changed, so that the grasping portion 212 is able to hold and firmly grasp the object to be grasped 02. Thus the versatility and flexibility of the linkage grasping assembly 20 is improved.

In one embodiment, the two opposing linkage grasping assemblies 20 are driven to rotate by the same driving assembly 40 to perform grasping or releasing operations. In other embodiment, the mounting base 70 is provided inside with a driving assembly which simultaneously drives the plurality of linkage grasping assemblies 20 to rotate, so as to perform simultaneous grasping or releasing operations. The driving assembly 40 may adopt the structure in the above-described embodiment, or may adopt a mechanism capable of realizing driving in the prior art. The driving assembly 40 drives the first rod 210 or the second rod 230 or 240 to rotate, so that the linkage grasping assembly 20 rotates relative to the mounting base 10.

In other embodiments, the grasping device adopts the linkage grasping assembly 20 described in any of the above embodiments to grasp the object, which has the advantages of the linkage grasping assembly 20 described in the corresponding embodiment, which will not be described here.

The foregoing respective technical features involved in the respective embodiments can be combined arbitrarily, for brevity, not all possible combinations of the respective technical features in the foregoing embodiments are described, however, to the extent they have no collision with each other, the combination of the respective technical features shall be considered to be within the scope of the description.

The foregoing implementations are merely specific the embodiment of the present disclosure, and are not intended to limit the protection scope of the present disclosure. It should be noted that any variation or replacement readily figured out by persons skilled in the art within the technical scope disclosed in the present disclosure shall all fall into the protection scope of the present disclosure. Therefore, the protection scope of the present disclosure shall be subject to the protection scope of the claims.

What is claimed is:

1. A grasping mechanism, comprising:
a base; and
at least two linkage grasping assemblies configured to cooperate with each other to grasp an object, each of the at least two linkage grasping assemblies comprising:
a grasping member comprising a grasping portion and a connecting portion connected to each other;
a first rod having a first end rotatably connected to the connecting portion and a second end rotatably connected to the base, a connecting line between a rotation center of the first end of the first rod and a rotation center of the second end of the first rod defining a first connecting line;
a second rod having a first end rotatably connected to the connecting portion and a second end rotatably connected to the base, a connecting line between a rotation center of the first end of the second rod and a rotation center of the second end of the second rod defining a second connecting line;
wherein the second rod is switchable between a first state in which a length of the second rod is kept constant and a second state in which the second rod is bent and deformed in such a way that the length of the first connecting line is different from the length of the second connecting line.

2. The grasping mechanism of claim 1, wherein
a first end of the connecting portion is rotatably connected to the first end of the first rod;
a second end of the connecting portion is rotatably connected to the first end of the second rod and is fixed to the grasping portion;
the second rod is bent and deformed in the second state in such a way that the length of the first connecting line is greater than the length of the second connecting line.

3. The grasping mechanism of claim 2, wherein
the second rod comprises a first finger root portion, an elastic portion, and a second finger root portion successively connected;
the first finger root portion is rotatably connected to the connection portion, the second finger root portion is rotatably connected to the base, and the elastic portion is bent and deformed in the second state.

4. The grasping mechanism of claim 3, wherein the elastic portion is an elastic metal sheet.

5. The grasping mechanism of claim 1, further comprising a driving assembly, wherein
each of the linkage grasping assemblies further comprises a connecting shaft and a first bearing;
the base defines a first mounting hole, the first bearing is mounted in the first mounting hole;
the connecting shaft is mounted on the first bearing and sealingly fits with the first bearing;
an end of the connecting shaft extends out of the first mounting hole, the second end of the first rod is fixed to the end of the connecting shaft;
the connecting shaft is connected to the driving assembly, and the driving assembly is configured to drive the connecting shaft to rotate so as to drive the first rod to rotate.

6. The grasping mechanism of claim 5, wherein
the first mounting hole comprises two sub-holes, the first bearing comprises two sub-bearings mounted in the two sub-holes, respectively;
the connecting shaft is mounted on the two sub-bearings, two ends of the connecting shaft extend out of the two sub-holes, respectively, and the second end of the first rod comprises two first mounting portions fixed to the two ends of the connecting shaft, respectively.

7. The grasping mechanism of claim 5, wherein the connecting shaft is connected to an inner ring of the first bearing by interference fit, and an outer ring of the first bearing is received in the first mounting hole by interference fit.

8. The grasping mechanism of claim 5, wherein
the driving assembly comprises a power source, a screw rod, a nut, at least two first transmission rods, and at least two second transmission rods;
the power source is connected to the screw rod;
the nut is sleeved on the screw rod and movable along the screw rod;
the first transmission rod has one end rotatably connected to the nut and the other end rotatably connected to the second transmission rod; and the second transmission rod is fixed to the connecting shaft.

9. The grasping mechanism of claim 5, wherein each of the linkage grasping assemblies further comprises a rotary shaft disposed on an outer wall of the base, the second end of the second rod is rotatably connected to the rotary shaft.

10. The grasping mechanism of claim 1, wherein an inner surface of the second rod is provided with a positioning groove or a positioning projection.

11. The grasping mechanism of claim 1, wherein the second rod is a straight rod or a bent rod.

12. The grasping mechanism of claim 1, wherein the grasping member further comprises a contacting portion connected to the grasping portion and located on a side corresponding to a grasping surface of the grasping portion.

13. The grasping mechanism of claim 1, wherein at least one of the first rod and the second rod has a length-adjustable structure.

14. The grasping mechanism of claim 1, wherein
the first end of the first rod comprises two opposing third mounting portions, and the first end of the second rod comprises two opposing fourth mounting portions;
the first end of the connecting portion is disposed between the two third mounting portions and rotatably connected to the two third mounting portions, respectively; and
the second end of the connecting portion is disposed between the two fourth mounting portions and rotatably connected to the two fourth mounting portions, respectively.

15. The grasping mechanism of claim 1, comprising two of the linkage grasping assemblies, wherein the two linkage grasping assemblies are opposingly arranged, and the two second rods are located on an inner side of the two linkage grasping assemblies.

16. A robot comprising a body and a grasping mechanism, the grasping mechanism comprising a base and at least two linkage grasping assemblies configured to cooperate with each other to grasp an object, each of the at least two linkage grasping assemblies comprising:
a grasping member comprising a grasping portion and a connecting portion connected to each other;
a first rod having a first end rotatably connected to the connecting portion and a second end rotatably connected to the base, a connecting line between a rotation center of the first end of the first rod and a rotation center of the second end of the first rod defining a first connecting line;
a second rod having a first end rotatably connected to the connecting portion and a second end rotatably connected to the base, a connecting line between a rotation center of the first end of the second rod and a rotation center of the second end of the second rod defining as a second connecting line;
wherein a length of the first connecting line is constantly different from a length of the second connecting line, or the second rod is switchable between a first state in which a length of the second rod is kept constant and a second state in which the second rod is bent and deformed in such a way that the length of the first connecting line is different from the length of the second connecting line.

17. The robot of claim 16, wherein
a first end of the connecting portion is rotatably connected to the first end of the first rod;
a second end of the connecting portion is rotatably connected to the first end of the second rod and is fixed to the grasping portion;
the length of the first connecting line is constantly greater than the length of the second connecting line; or the second rod is bent and deformed in the second state in such a way that the length of the first connecting line is greater than the length of the second connecting line.

18. The robot of claim 17, wherein
the second rod comprises a first finger root portion, an elastic portion, and a second finger root portion successively connected;
the first finger root portion is rotatably connected to the connection portion, the second finger root portion is rotatably connected to the base, and the elastic portion is bent and deformed in the second state.

19. A grasping device comprising a mounting base and a plurality of linkage grasping assemblies, wherein the plurality of linkage grasping assemblies are disposed in pairs facing each other and are arranged on the mounting base in an array, the two opposing linkage grasping assemblies are configured to cooperate with each other to grasp an object, and each of the plurality of linkage grasping assemblies comprising:
a grasping member comprising a grasping portion and a connecting portion connected to each other;
a first rod having a first end rotatably connected to the connecting portion and a second end rotatably connected to the mounting base, a connecting line between a rotation center of the first end of the first rod and a rotation center of the second end of the first rod being defining a first connecting line;
a second rod having a first end rotatably connected to the connecting portion and a second end rotatably connected to the mounting base, a connecting line between a rotation center of the first end of the second rod and a rotation center of the second end of the second rod defining a second connecting line;
wherein a length of the first connecting line is constantly different from a length of the second connecting line, or the second rod is switchable between a first state in which a length of the second rod is kept constant and a second state in which the second rod is bent and deformed in such a way that the length of the first connecting line is different from the length of the second connecting line.

20. The grasping device of claim 19, wherein
a first end of the connecting portion is rotatably connected to the first end of the first rod;
a second end of the connecting portion is rotatably connected to the first end of the second rod and fixed to the grasping portion;
the length of the first connecting line is constantly greater than the length of the second connecting line; or the second rod is bent and deformed in the second state in such a way that the length of the first connecting line is greater than the length of the second connecting line.

* * * * *